(12) United States Patent
Kuhrts

(10) Patent No.: US 8,883,225 B2
(45) Date of Patent: *Nov. 11, 2014

(54) WATER-SOLUBLE PHARMACEUTICAL COMPOSITIONS OF HOPS RESINS

(71) Applicant: Bioactives, Inc., Novato, CA (US)

(72) Inventor: Eric H. Kuhrts, Novato, CA (US)

(73) Assignee: Bioactives, Inc., Bodega, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/736,513

(22) Filed: Jan. 8, 2013

(65) Prior Publication Data

US 2014/0023599 A1 Jan. 23, 2014

(51) Int. Cl.

| A01N 65/00 | (2009.01) |
|---|---|
| A61K 8/35 | (2006.01) |
| A61Q 5/10 | (2006.01) |
| A61K 8/60 | (2006.01) |
| A61K 31/122 | (2006.01) |
| A61K 8/97 | (2006.01) |
| A61K 8/86 | (2006.01) |
| A61Q 11/00 | (2006.01) |
| A61K 36/185 | (2006.01) |
| A61K 8/04 | (2006.01) |

(52) U.S. Cl.
CPC ......... *A61K 36/185* (2013.01); *A61K 8/35* (2013.01); *A61Q 5/10* (2013.01); *A61K 8/604* (2013.01); *A61K 31/122* (2013.01); *A61K 8/97* (2013.01); *A61K 8/86* (2013.01); *A61K 8/355* (2013.01); *A61Q 11/00* (2013.01); *A61K 8/042* (2013.01)
USPC ........................................................... 424/725

(58) Field of Classification Search
None
See application file for complete search history.

(56) References Cited

U.S. PATENT DOCUMENTS

| 4,338,348 | A | 7/1982 | Muller |
|---|---|---|---|
| 4,640,841 | A | 2/1987 | Forster et al. |
| 5,446,587 | A | 8/1995 | Kang et al. |
| 5,707,612 | A | 1/1998 | Zofchak et al. |
| 5,719,704 | A | 2/1998 | Shiraishi et al. |
| 5,757,470 | A | 5/1998 | Dewa et al. |
| 5,978,072 | A | 11/1999 | Nojima |
| 6,020,019 | A | 2/2000 | Ting et al. |
| 6,048,562 | A | 4/2000 | Mandralis et al. |
| 6,236,449 | B1 | 5/2001 | Tanitsh |
| 6,285,443 | B1 | 9/2001 | Wangler et al. |
| 6,350,785 | B2 | 2/2002 | Gehlsen |
| 6,452,662 | B2 | 9/2002 | Mulkens et al. |
| 6,583,855 | B2 | 6/2003 | Krikke et al. |
| 6,689,388 | B2 | 2/2004 | Kuhrts |
| 8,071,136 | B2 | 12/2011 | Kuhrts |
| 2003/0091656 | A1 | 5/2003 | Kuhrts |
| 2003/0203050 | A1 | 10/2003 | Sherwood et al. |
| 2004/0137096 | A1 | 7/2004 | Kuhrts |
| 2004/0141938 | A1 | 7/2004 | Gallinat et al. |
| 2005/0031572 | A1 | 2/2005 | Gallinat et al. |
| 2006/0134024 | A1 | 6/2006 | Trivedi et al. |

FOREIGN PATENT DOCUMENTS

| FR | 2590589 | 5/1987 |
|---|---|---|
| GB | 2072657 | 10/1981 |
| JP | 63211219 | 9/1988 |
| JP | 5335208 | 12/1993 |
| JP | 10025232 | 1/1998 |
| JP | 2001-017138 | 1/2001 |
| WO | WO 2005/089104 | 9/2005 |

OTHER PUBLICATIONS

Answers.com; Hops; 8 Pages; 2008.
Wolfe et al.; Gastrointestinal Toxicity of Nonsteroidal Antinflammatory Drugs; New England Jornal of Medicine; Jun. 17, 1999; pp. 1888-1899; vol. 340, No. 24.
Brooks et al; Interpreting the Clinical Significance of the Differential Inhibition of Cycloxygenase-I and Cyclooxygenase-2; British Society for Rheumatology; 1999; pp. 779-788; vol. 38.
Warner et al; Nonsteroid Drug Selectivities for Cyclooxygenase-I Rather then Cycloxgenase-2 are associated with Human Gastrointestinal Toxicity; A Full In Vitro Analysis; Proc. Natl. Acad. Sci. USA; Jun. 1999; pp. 7563-7568; vol. 96.
Yasukawa et al; Humulon, A Bitter in the Hop, Inhhibits Tumor Promotion by 12-0-Teradecanoylphorbol-13-Acetate in Two-Stage Carcinogenesis in Mouse Skin; Oncology; 1995; pp. 156-158; vol. 52.
Yamamoto, et al; Suppression of Cycloxygenase-2 Gene Transcription by Humlon of Beer Hop Extract Studied with Reference to Glucocorticoid; Federation of European Biochemical Societies; 2000; pp. 103-106; vol. 465.
Wallace et al; NSAID-Induced Gastric Damage in the Rat: Requirement for Inhibition of Both Cyclooxygenase-1 and Cyclooxygenase-2; Gastroenterology; 2000; pp. 706-714; vol. 119.
Patrignani Biochemical and Pharmacological Characterization of the Cyclooxytenase Activity of Human Blood Prostaglndin Endoperoxide Synthases; Journal of Pharmacology and Experimental Therapeutics; 1994; pp. 1705-1711; vol. 271, No. 3.
Srinivasan, et al.; "Contributions to the Antimicrobial Spectrum of Hop Constituents"; Economic Botany, vol. 58, Issue 1, Supplement pp. S230-S238; published 2004.

*Primary Examiner* — Michael Meller
(74) *Attorney, Agent, or Firm* — Thorpe North & Western LLP

(57) ABSTRACT

The present invention is drawn to water-soluble compositions for providing hops constituents, particularly alpha acids, iso-alpha acids, and beta acids. A pharmaceutical gel composition can comprise a hops extract and a surfactant. Such compositions can be formulated into products for various therapeutic applications, including oral and topical uses. Such compositions can also be dissolved in water to yield a clear solution containing more dilute hops acids. The invention also provides methods of treatment comprising administering water-soluble hops compositions. The present invention is also drawn to methods for making water-soluble preparations of hops constituents.

11 Claims, No Drawings

WATER-SOLUBLE PHARMACEUTICAL COMPOSITIONS OF HOPS RESINS

The present application is a continuation of U.S. patent application Ser. No. 13/311,288, filed on Dec. 5, 2011, which is a continuation of U.S. patent application Ser. No. 11/409,521, filed on Apr. 21, 2006, both of which are incorporated herein by reference.

FIELD OF THE INVENTION

This invention relates to unique pharmaceutical compositions comprising water soluble extracts of hops resins, and methods for preparation of such compositions. The invention also relates to methods for treating conditions in a subject using water-soluble hops compositions.

BACKGROUND OF THE INVENTION

Many botanical substances contain chemicals that have been found to be useful for the therapeutic treatment of various medical conditions. Since these chemicals are often present in very small amounts, techniques have been developed to extract these substances and to concentrate the therapeutically active agents. Various methods are available for extraction and purification of such substances, including the use of organic solvents, microwave systems, and supercritical $CO_2$ extraction. Organic solvent-based extractions utilize added solvents that are evaporated to form a concentrated extract, which results in a damp, pasty mass that is typically further spray-dried onto a carrier for delivery. Alternatively, supercritical $CO_2$ extraction is another method of collecting such extracts. This extraction method yields a thick, high viscosity resin, oil, or other fluid-like material that can have a honey-like consistency.

One pharmaceutically useful botanical substance is the extract of hops (*Humulus lupulus* L.). Hops cone flowers contain a variety of active agents, including alpha acids, iso-alpha acids, and beta acids, as well as a number of flavonoids and essential oils. Humulone, one of the alpha acids found in hops, has been demonstrated to suppress cyclooxygenase-2 activity, inhibit angiogenesis, and decrease bone loss. Some other biologically relevant properties of hops constituents include anti-inflammatory, antibacterial, antiviral, antifungal, estrogenic, anti-oxidant, anti-allergenic, anti-carcinogenic, and anti-proliferative properties.

As with other botanical substances, dried hops flowers contain very small amounts of alpha acids. Supercritical $CO_2$ extraction and other solvent-based extractions of dried hops cones produce a thick, high-viscosity resin that can contain a high percentage of active hops constituents. While extraction is an effective means of providing alpha and beta acids in a highly concentrated form, the resulting extracts have very low solubility in water. This property can make digesting such extracts difficult, resulting in delayed absorption of the acids and delayed onset of certain therapeutic effects. It would therefore be useful to provide the primary constituents of hops extracts in formulations that are soluble in water. In addition, methods of making such formulations from hops extract resin would be desirable.

SUMMARY OF THE INVENTION

It has been recognized that it would be advantageous to be able to formulate hops extract into water-soluble forms that can be used in oral or topical formulations. In accordance with this, a pharmaceutical gel composition can comprise from 0.2 wt % to 70 wt % hops extract, and from 30 wt % to 99.8 wt % non-ionic surfactant. The gel composition can be free of visible particulates and be water-soluble. A clear pharmaceutical solution can be prepared therefrom by dissolving in water to yield the clear solution. The clear solution can comprise from 0.0005 wt % to 24.5 wt % alpha acids and from 0.0001 wt % to 12.5 wt % beta acids.

In these embodiments, the gel composition or the clear pharmaceutical solution can be formulated into various product forms such as toothpastes, creams, ointments, lotions, salves, nasal mists, and oral rinses.

In another embodiment, a method of making a water-soluble pharmaceutical gel composition of hops extract can comprise the steps of heating a water-soluble non-ionic surfactant in a container to a temperature of about 90° F. to 250° F., while mixing the surfactant until it is clear; heating a hops extract to a temperature of about 90° F. to 120° F. (a higher temperature, e.g., up to 250° F., may be desirable if the goal is isomerization of the alpha acids); and mixing an amount of the hops extract with the surfactant so as to constitute from 0.2 wt % to 70 wt % hops extract and from 30 wt % to 99.8 wt % surfactant. The hops extract can be sufficiently dispersed or dissolved in the surfactant so that the gel composition contains no visible particles of hops extract.

In another embodiment, a method of making a clear pharmaceutical solution can comprise dissolving or finely dispersing the gel composition described above, such as in water or an aqueous solvent system, such that the clear pharmaceutical solution comprises from 0.0005 wt % to 24.5 wt % alpha acids and from 0.0001 wt % to 12.5 wt % beta acids.

DETAILED DESCRIPTION OF THE PREFERRED EMBODIMENT(S)

Before particular embodiments of the present invention are disclosed and described, it is to be understood that this invention is not limited to the particular process and materials disclosed herein, as such can vary to some degree. It is also to be understood that the terminology used herein is used for the purpose of describing particular embodiments only and is not intended to be limiting, as the scope of the present invention will be defined only by the appended claims and equivalents thereof.

It is to be noted that, as used in this specification and the appended claims, the singular forms "a," "an," and "the" include plural referents unless the context clearly dictates otherwise.

As used herein, "administration," and "administering" refer to the manner in which a drug, formulation, or composition is introduced onto or into the body of a subject. Administration can be accomplished by various art-known routes such as topical, oral, parenteral, transdermal, inhalation, etc. Thus, topical administration can be achieved by applying to intact or damaged skin, or to a tooth, gums, tongue, or other oral surface of a subject. An oral administration can be achieved by swallowing, chewing, or sucking an oral dosage form comprising active agent(s). Parenteral administration can be achieved by injecting a composition intravenously, intra-arterially, intramuscularly, intrathecally, or subcutaneously, etc. Transdermal administration can be accomplished by applying, pasting, rolling, attaching, pouring, pressing, rubbing, etc., of a transdermal preparation onto a skin surface. In some cases, it can be desirable to administer a composition for the purpose of having a therapeutic or hygienic effect in the oral cavity itself. In these cases, administration can be achieved by placing an amount of the composition into the mouth and spreading the composition on the desired oral surfaces either by moving the tongue, or by using an appropriate instrument such as a brush or a swab. These and additional methods of administration are well known in the art.

The terms "effective amount," and "sufficient amount" can be used interchangeably and refer to an amount of an ingredient which, when included in a composition, is sufficient to achieve an intended compositional or physiological effect. Thus, a "therapeutically effective amount" refers to a nontoxic, but sufficient amount of an active agent, to achieve therapeutic results in treating a condition for which the active agent is known to be effective. Various biological factors can affect the ability of a substance to perform its intended task. Therefore, a "sufficient amount" or a "therapeutically effective amount" can be dependent on such biological factors. Further, while the achievement of therapeutic effects can be measured by a physician or other qualified medical personnel using evaluations known in the art, it is recognized that individual variation and response to treatments can make the achievement of therapeutic effects a subjective decision. In some instances, a "sufficient amount" of an active agent can achieve a therapeutic effect that is measurable by the subject receiving the active agent. The determination of an effective amount is well within the ordinary skill in the art of pharmaceutical, medicinal, and health sciences.

The terms "supercritical carbon dioxide" and "supercritical $CO_2$" each refers to carbon dioxide gas that has been heated and pressurized until it is beyond its critical state, e.g., above 310° C. and 73 atmospheres. Gases in this state have been found to be excellent solvents, possessing a pressure-tunable dissolving power, liquid-like density, and gas-like transport properties. The term "supercritical carbon dioxide extraction" refers to a separation process using supercritical $CO_2$ as a solvent. It should be noted that there are various other steps that can be carried out to modify the percentages of various constituents of an extract prepared using supercritical carbon dioxide extraction (as well as other extraction methods), such as fractionation, TLC (thin layer chromatography), etc., The term "alpha acid(s)" refers to humulone, cohumulone, adhumulone, dihydrohumulone, dihydrocohumulone, dihydroadhumulone, or any mixture thereof. This term does not refer to the various isomers of these three compounds, however. Instead, the term "iso-alpha acid(s)" refers to iso-humulone, iso-cohumulone, iso-adhumulone, trans-iso-humulone, cis-iso-humulone, trans-iso-cohumulone, cis-iso-cohumulone, cis-iso-adhumulone, trans-iso-adhumulone, dihydro-iso-humulone, and dihydro-iso-adhumulone, or any mixture thereof.

The term "beta acid(s)" refers to lupulone, colupulone, adlupulone, prelupulone, postlupulone, or any mixture thereof.

The term "surfactant" refers to substances comprising typically amphipathic molecules that have the effect of decreasing surface tension in certain fluids, for example reducing the tension at a lipid/water interface. As used herein, a "non-ionic surfactant" is a surfactant that tends to have no net charge in neutral solutions.

As used herein, "solution" can refer to a preparation in which a first composition is intermixed with a second composition. For the purposes of the present invention, the degree of intermixing can be such that the first composition is present in the solution as particles that are too small to be visible by the naked eye. These particles can be individual ions, atoms, or molecules, or assemblages of such units that are small enough to disperse throughout the preparation into a substantially random spatial distribution. Thus, the term "solution" encompasses both solubilized liquid mixtures or finely dispersed liquid mixtures, provided the "solution" appears clear to the naked eye.

The term "clear," as used herein in reference to the compositions of the present invention, shall be understood to describe the visual appearance that such solutions possess, i.e. that, when viewed in a transparent container with the naked eye, objects can be seen through the solution, but no particulate matter can be seen in the solution itself. Under this definition, "clear" can describe colorless solutions as well as those having color of a hue and intensity that does not prevent it from being seen through, e.g., pale color.

As used herein, "subject" refers to an animal, such as a mammal, that can benefit from the administration of the compositions or formulations of the present invention. Most often, the subject will be a human.

The term "about" when referring to a numerical value or range is intended to encompass the values resulting from experimental error that can occur when taking measurements.

As used herein, a plurality of items, structural elements, compositional elements, and/or materials can be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data can be presented herein in a range format. It is to be understood that such a range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight range of about 1 wt % to about 20 wt % should be interpreted to include not only the explicitly recited concentration limits of about 1 wt % to about 20 wt %, but also to include individual concentrations such as 2 wt %, 3 wt %, 4 wt %, and sub-ranges such as 5 wt % to 15 wt %, 10 wt % to 20 wt %, etc.

In accordance with these definitions and recognitions, the present invention is drawn to pharmaceutical gel compositions comprising 0.2 wt % to 70 wt % of a hops extract and 30 wt % to 99.8 wt % of a non-ionic surfactant. Though any extract can be used, preferably, the extract can be a resin extract, such as that produced using $CO_2$ extraction or other solvent extraction methods. According to one embodiment, a pharmaceutical gel composition can include from 0.25 wt % to 49.5 wt % of a combination of alpha acids and iso-alpha acids, and from 0.05 wt % to 25 wt % beta acids. The non-ionic surfactant can be a single mono-, di-, or triglyceride, mono- or di-fatty acid ester of polyethylene glycol, sorbitan fatty acid ester, polyglycolyzed glyceride, triblock copolymer, or a mixture thereof. According to a particular embodiment, the non-ionic surfactant can be polyoxyl castor oil.

According to another embodiment of the invention, a pharmaceutical composition can comprise the pharmaceutical gel composition dissolved in water or aqueous solvent system to yield a clear solution containing from 0.0005 wt % to 24.5 wt % alpha acids and from 0.0001 wt % to 12.5 wt % beta acids. In more particular aspects of this embodiment, the composition can be formulated into a product further comprising additives such as flavoring agents and coloring agents.

This being stated, the present invention is directed to methods and compositions for providing therapeutically active constituents of hops, as well methods of making such compositions. Pharmaceutically useful botanical compounds are often only present in low amounts in their respective plants. The cone flower of hops (*Humulus lupulus* L.) is no exception, and has been found to contain a number of agents with possible therapeutic applications. For example, dried hops flowers contain small amounts of alpha acids and beta acids. To collect a more concentrated form of the active ingredients in hops, these ingredients can be extracted and purified by various techniques, including organic solvent extraction, microwave extraction, or supercritical $CO_2$ extraction. While the present invention can utilize hops extract collected by any of these or other techniques suitable for extracting plant materials, extracts produced by supercritical $CO_2$ extraction are preferred in some embodiments for use in accordance with this invention. This process involves passing supercritical carbon dioxide gas through hops powder, thereby dissolving the constituents into the gas. The gas is then recovered and depressurized, causing the dissolved materials to precipitate out. If desired, the recovered gas can be re-pressurized and recycled back through the hops for further extraction.

One advantage of supercritical $CO_2$ extraction over solvent-based techniques is that substantially no solvent residues remain with the extract. The resulting product is a thick, high-viscosity resin, oil, or other fluid-like material, which can be engineered to produce a very high percentage of alpha acids, a much lower percentage of beta acids, and essentially no essential oils. Processes such as fractionation with a mineral salt or oxide/hydroxide, e.g., magnesium oxide, TLC (thin layer chromatography), etc., can be used to generate desired levels of these constituents. For example, the hops resin produced by supercritical $CO_2$ extraction can contain 60 wt % or more alpha acids, compared to 5 wt % to 15 wt % typically present in extracts from organic solvents, and 1 wt % to 5 wt % present in dried hops cones. The extract can then be fractionated so as to achieve a resin containing over 80 wt % alpha acids. Supercritical $CO_2$ extraction can therefore yield a resin that is much more potent than dried hops flowers. Such a resin will contain alpha acids, iso-alpha acids, and/or beta acids. In one embodiment, all three types of extracted acids can be present, or in another embodiment, alpha acids can be substantially converted to iso-alpha acids within the extract. If the desire is to convert the alpha acids to more iso-alpha acids, then the alpha acids can be isomerized by heating the high-viscosity extract with potassium hydroxide or another mineral salt in aqueous solution. The resulting hops extract yields iso-alpha acids.

Alpha acids and beta acids can be useful in clinical applications where reduction of inflammation, inhibition of angiogenesis, prevention or treatment of cancer, or decreased bone loss is desired. In addition, hops acids are known to have significant anti-microbial activity. One example of this is found in the brewing arts, where for centuries hops have been added to beer, not only to add astringency and aromatic flavor, but to preserve the beer from spoilage during storage. This effect is due to strong inhibition of gram-positive bacteria by iso-alpha acids and beta acids. Hops acids, particularly beta acids, have been shown to inhibit growth in a number of types bacteria that inhabit the human body such as gastritis-causing *Helicobacter pylori*, as well as oral *Streptococcus* bacteria such as *Streptococcus mutans, Streptococcus sanguis*, and *Streptococcus salivarius*.

Utilizing hops acids for these and other therapeutic indications can be facilitated by providing them in an aqueous form. However, the principal high-percentage sources for these acids—hops extract resins—are largely water-insoluble. Therefore, in accordance with these recognitions, the present invention provides a method for making a water-soluble hops extract composition. It has been discovered that non-ionic surfactants can be used to increase or provide the solubility of hops acids in certain aqueous formulations. Therefore, a method in accordance with the present invention can comprise the steps of mixing a hops extract with a water-soluble non-ionic surfactant. More particularly, the process can include heating a volume of non-ionic surfactant while stirring or mixing it until cloudiness of the surfactant dissipates. To achieve this, the surfactant can be heated to a temperature of from 90° F. to 250° F. Likewise, a hops extract resin can also be heated and mixed to a temperature of from 90° F. to 120° F. (or up to 250° F. if the goal is isomerization of the alpha acids). In this state, the desired amount of heated hops extract can be mixed or stirred into a desired amount of heated surfactant. The resulting composition can be a water-soluble gel that is free of any cloudiness or visible particulates, and remains so after it has been allowed to cool.

The amounts of extract and surfactant used will depend on the amount of hops extract—or more particularly, of hops acids—desired to be present in the product composition. If creating a composition having a certain hops acids content is the desired goal, then the amount of hops extract to be used will further depend on the concentrations of those acids contained in the hops extract. The range of relative proportions of extract and surfactant used can be limited to one extent by the minimum amount of hops acids that will be useful in the resulting composition or formulations made from it, and to the opposite extent by the minimum amount of surfactant needed to make the resulting composition water-soluble. According to one embodiment of the invention, an amount of hops extract can be used so as to constitute from 0.2 wt % to 70 wt % of the resulting composition, with an amount of surfactant being used so as to constitute the balance of the resulting composition, i.e. from 30 wt % to 99.8 wt %.

The novel combination of hops extract and a non-ionic surfactant provided by this invention can be an effective vehicle for administering hops acids. Hops extracts typically contain both alpha and iso-alpha acids, so in a particular aspect, the composition of the present invention can also include a combination of alpha acids and iso-alpha acids. In a more particular aspect, the composition can include from 0.25 wt % to 49.5 wt % of a combination of alpha and iso-alpha acids and from 0.05 wt % to 25 wt % beta acids. For certain applications a composition with a higher iso-alpha acid content can be desirable. As described above, alpha acids can be converted to iso-alpha acids under certain conditions. The conversion can be total, resulting in a product in which nearly all alpha acids have been converted to iso-alpha acids or other derivates and little to no alpha acids remain. Therefore, in another particular aspect of the invention, the composition can include from 0.25 wt % to 49.5 wt % iso-alpha acids and be substantially free of alpha acids.

In the compositions provided by the present invention, the hops extract resin is rendered water-soluble largely through mixture with the non-ionic surfactant. Any surfactant that has no net charge in neutral solutions can conceivably be used in accordance with the present invention. Water-soluble non-ionic surfactants are preferred. Particularly, suitable non-ionic surfactants for the purposes of the invention can be monoglycerides, diglycerides, triglycerides, mono-fatty acid esters of polyethylene glycol, di-fatty acid esters of polyethylene glycol, sorbitan fatty acid esters, polyglycolyzed glycerides, triblock copolymers, and mixtures thereof. Examples of non-ionic water-soluble monoglycerides, diglycerides, and triglycerides include propylene glycol dicaprylate/dicaprate, medium-chain monoglycerides and diglycerides, medium-chain triglycerides, long-chain monoglycerides, polyoxyethylene castor oil, their derivatives, and mixtures thereof. Non-ionic water-soluble mono-fatty acid esters and di-fatty acid esters of polyethyelene glycol include d-alpha-tocopheryl polyethyleneglycol 1000 succinate, polyethyleneglycol 660 12-hydroxystearate, polyoxyl oleate and stearate, and their derivatives. Polyglycolyzed glycerides include polyoxyethylated oleic glycerides, polyoxyethylated linoleic glycerides, polyoxyethylated caprylic/capric glycerides, and their derivatives. In one embodiment of the present invention, the non-ionic surfactant is a polyoxyl castor oil. Effective polyoxyl castor oils can be synthesized by reacting either castor oil or hydrogenated castor oil with varying amounts of ethylene oxide. Polyoxyl 35 castor oil is available under the trade names Cremophor EL (BASF, Inc., Ludwigshafen, Germany) and Etocas 35 (Croda, Inc., Parsippany, N.J., USA), and is a mixture of 83% relatively hydrophobic and 17% relatively hydrophilic components. The major component of the relatively hydrophobic portion is glycerol polyethylene glycol ricinoleate, and the major components of the relatively hydrophilic portion are polyethylene glycols and glycerol ethoxylates. Polyoxyl 40 hydrogenated castor oil, is available as Cremophor RH 40 (BASF, Inc.), and comprises approximately 75% relatively hydrophobic components, of which a major portion is glycerol polyethylene glycol 12-oxystearate.

The gel compositions provided by the present invention can be formulated directly into a number of products designed for a variety of uses in which administration of hops acids is desired. Such products can include formulations for oral application such as toothpastes and gels, as well as oral rinses. Such products can alternatively include formulations for topical application, such as creams, ointments, and lotions. In addition to the surfactant, the gel compositions of the present invention can include additives typically used in formulating certain products. For example, where the composition is to be formulated into a toothpaste, it can additionally include abrasives, bleaching agents, odorants, flavoring agents, coloring agents, sweeteners, desensitizing agents, sodium bicarbonate or other bicarbonates, anti-tartar agents, detergents, binding agents, or any combination thereof. For formulation into topically-applied products such as creams, ointments, and lotions, the composition can additionally include emulsifiers, vitamins, minerals, preservatives, moisturizers (such as lanolin or glycerin), hormones, fragrances, coloring agents, diethanolamines, or any combination thereof. It should be understood that these lists of additives are intended to be illustrative rather than exhaustive. Those having skill in the relevant arts will be aware of which of these or other additives not listed here can be appropriately used for a particular product, and any such additives can be included in accordance with the present invention.

For certain therapeutic applications, a more dilute aqueous solution of hops acids can be desired. Therefore, the present invention also provides pharmaceutical compositions comprising an amount of the hops extract gel composition dissolved in water, yielding a clear solution. Such a solution will therefore contain certain levels of hops constituents, including alpha and beta acids. The amount of these constituents will naturally depend on the amount of the gel composition used as well as its chemical makeup. The color of the solution can range from yellow to substantially colorless, also depending on the amount of hops extract dissolved therein. In one embodiment, the composition can include from 0.0005 wt % to 24.5 wt % alpha acids and from 0.0001 wt % to 12.5 wt % beta acids. Such a composition could be useful in applications that call for more dilute hops acids in a low-viscosity preparation. For example, quite low levels of hops acids—particularly beta acids—can constitute an effective anti-bacterial oral treatment, serving to combat plaque buildup and gum disease. Therefore, one exemplary use for water-based preparations such as provided by this embodiment can be as a base ingredient for an oral rinse. Other types of products incorporating this composition are also possible, as will be recognized by those having skill in the relevant art. In a more particular aspect, the composition can include additives such as flavoring agents, sweeteners, coloring agents, odorants, and mixtures thereof.

The compositions of the present invention are different than those currently known for at least two reasons, both of which contribute to enhancing therapeutic effects when delivered to subjects. First, these compositions are in a liquid water-soluble form. As such, they can be incorporated into a number of products designed for administering therapeutically active agents. These include not only products intended for application on body surfaces such as skin, teeth, tongue, and gums, but also liquid products for oral administration such as elixirs. Also, the compositions of the present invention contain lower concentrations of alpha acids than are typically found in pure hops extract. High concentrations of alpha acids such as are found in hops extract resins can be associated with undesirable side effects, such as stomach gas and nausea. Administering products that contain lower concentrations of these acids can decrease or eliminate these side effects, resulting in higher subject compliance in using them.

By providing hops acids in a water-soluble composition, the present invention also provides methods for increasing their bioavailability when ingested by a subject. The water-soluble nature of these compositions renders them able to enter the aqueous phase of the subject's intestinal contents, aiding digestion and subsequent absorption through the intestinal lining and into the bloodstream.

The compositions of the present invention have great versatility in their application. As noted above, the widely useful properties of hops means that the compositions can be used for treating various cancers, inflammatory conditions, tooth decay, gum disease, as antibiotics, as anti-fungals, as anti-viral agents, for treatment of protozoa or various food born pathogens, and essentially any disease or malady that hops has been found to ameliorate. Therefore, the present invention provides methods for treating such conditions in a subject, comprising administering water-soluble hops extract compositions to the subject.

In one embodiment, a method of treating an oral cavity of a subject can comprise rinsing the oral cavity of a subject with an aqueous solution containing hops extract. Such treatment can be to treat tooth decay, gingivitis, infection, oral diseases, or for prophylactic treatment. Such a method could involve a subject accepting a small amount of the solution or a product made therefrom into his/her mouth, and holding it there while using movements of the tongue to swish the solution around so that it is made to contact the dental and gingival surfaces. This could be practiced as a part of the subject's daily hygiene regimen; for example, the subject could rinse with the solution or product before and/or after brushing the teeth. Alternatively, or in addition to the practice, the subject can use the rinse at other times of the day, such as after meals. In another embodiment, a method of treating an oral cavity of a subject can comprise brushing the teeth and gums with a toothpaste or tooth gel that includes a hops extract gel composition. Using water-soluble hops extract compositions such as provided by this invention could decrease or slow tooth decay and the processes that lead to decay in a subject. It is also anticipated that its use could prevent or delay the onset of tooth decay in a subject not already exhibiting that condition.

EXAMPLES

The following Examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following Examples provide further detail in connection with what are presently deemed to be the most practical and preferred embodiments of the invention.

Example 1

Two hundred milliliters of polyoxyl 40 Castor Oil (USP/NF) is warmed slightly while stirring until clear. Forty grams of a commercially available supercritical carbon dioxide hops extract containing 60 wt % alpha acids (24 g of alpha acids) is warmed to about 100° F. and poured into the castor oil with continued stirring until a golden yellow clear gel is achieved. HPLC analysis of this gel reveals it to contain 10.82 wt % alpha acids and 3.2 wt % beta acids, and is pourable after cooling, exhibiting a lower viscosity than the native resin.

Example 2

The gel produced in Example 1 is added to 80 mL of warm water and becomes completely dissolved after mixing, forming a pale yellow solution with no undissolved particles of resin. Analysis of this solution by HPLC reveals it to contain a level of alpha acids of 8.49 wt %.

Example 3

Fifty milliliters of polyoxyl 40 Castor oil (USP/NF) is warmed and mixed until clear as above. To this is added 10 grams of a warmed $CO_2$ extract of hops resin that has been further fractionated to contain 80 wt % alpha acids. A clear yellow water-soluble gel is formed that when analyzed, is found to contain 5.6 wt % alpha acids and 0.8 wt % beta acids.

Example 4

Five grams of the gel from Example 3 is mixed with 200 mL water making a dilute, pale yellow mouth rinse. HPLC analysis of this solution reveals it contains 0.14 wt % alpha acids and 0.014 wt % beta acids. This solution is completely clear of undissolved particles of resin or other matter.

Example 5

The dilute solution of alpha and beta acids from Example 4 is further diluted in water to contain 5 μg/ml of beta acids, which would exceed the minimum inhibitory concentration (MIC) of beta acid for inhibiting growth of *Streptococcus mutans*, the primary bacteria responsible for causing dental caries in humans. This solution is then flavored and sweetened to produce an oral rinse to treat plaque and tooth decay.

Example 6

A mixture of polyoxyl 40 Castor Oil (USP/NF) is warmed slightly while stirring until clear. A commercially available supercritical carbon dioxide hops extract containing 60% alpha acids is warmed to about 100° F. and poured into the castor oil with continued stirring until a very pale yellow clear gel is achieved. The resultant gel has less than 1 wt % of alpha acids and less than 1 wt % beta acids.

While the invention has been described with reference to certain preferred or illustrative embodiments, those skilled in the art will appreciate that various substitutions, modifications, changes, or omissions can be made without departing from the spirit of the invention. It is therefore intended that the invention be limited only by the scope of the appended claims.

What is claimed is:

1. A method of making a water-soluble pharmaceutical gel composition of isomerized hops extract, comprising the steps:
    heating a water-soluble non-ionic surfactant in a container to a temperature of about 90° F. to about 250° F., while mixing the non-ionic surfactant until it is clear, wherein the non-ionic surfactant is selected from the group consisting of monoglycerides, diglycerides, triglycerides, mono-fatty acid esters of polyethylene glycol, di-fatty acid esters of polyethylene glycol, sorbitan fatty acid esters, polyglycolyzed glycerides, triblock copolymers, and mixtures thereof;
    heating a hops extract to a temperature of about 120° F. to 250° F. such that isomerization of the hops extract occurs to yield isomerized hops; and
    mixing an amount of the hops extract which includes the isomerized hops extract with the non-ionic surfactant so as to yield from 0.2 wt % to 70 wt % hops extract which includes the isomerized hops extract and from 30 wt % to 99.8 wt % non-ionic surfactant,
    wherein the hops extract which includes the isomerized hops extract is sufficiently dispersed or dissolved in the non-ionic surfactant to yield the water-soluble pharmaceutical gel composition of isomerized hops extract which contains no visible particles.

2. A method as in claim 1, wherein the step of heating the water-soluble non-ionic surfactant includes the step of stirring or mixing during the heating step.

3. A method as in claim 1, wherein the step of heating the hops extract includes the step of stirring or mixing during the heating step.

4. A method as in claim 1, wherein the non-ionic surfactant is selected from the group consisting of monoglycerides, diglycerides, triglycerides, and mixtures thereof.

5. A method as in claim 1, wherein the non-ionic surfactant includes polyoxyl castor oil.

6. A method as in claim 1, wherein the water-soluble pharmaceutical gel composition is formulated into a product from selected from the group consisting of toothpastes, creams, ointments, lotions, salves, nasal mists, and oral rinses.

7. A method as in claim 1, further comprising the step of including an additive selected from the group consisting of flavoring agents, sweeteners, coloring agents, odorants, and mixtures thereof.

8. A method of making a clear pharmaceutical solution, comprising dissolving or finely dispersing the water-soluble pharmaceutical gel composition of isomerized hops extract prepared in accordance with claim 1 in water such that the clear pharmaceutical solution is formed.

9. A method as in claim 8, wherein the clear pharmaceutical solution comprises: (a) from 0.0005 wt % to 24.5 wt % alpha acids including isomerized alpha acids; and (b) from 0.0001 wt % to 12.5 wt % beta acids.

10. A method as in claim 9, wherein the clear pharmaceutical solution is pale in color.

11. A method as in claim 8, further comprising the step of including an additive selected from the group consisting of flavoring agents, sweeteners, coloring agents, odorants, and mixtures thereof.

* * * * *